United States Patent
Shimp

(10) Patent No.: US 6,911,045 B2
(45) Date of Patent: Jun. 28, 2005

(54) BIO-IMPLANT INSERTION INSTRUMENT

(75) Inventor: Lawrence A. Shimp, Morganville, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 10/407,113

(22) Filed: Apr. 4, 2003

(65) Prior Publication Data

US 2003/0225414 A1 Dec. 4, 2003

Related U.S. Application Data

(60) Provisional application No. 60/370,015, filed on Apr. 4, 2002.

(51) Int. Cl.[7] .................................................. A61F 2/44
(52) U.S. Cl. .................................. 623/17.13; 623/12.11
(58) Field of Search .......................... 623/17.11, 17.12, 623/17.13, 17.14, 17.15, 17.16, 23.17; 606/100; 433/169, 170

(56) References Cited

U.S. PATENT DOCUMENTS

| | | | | |
|---|---|---|---|---|
| 4,205,400 A | * | 6/1980 | Shen et al. | 623/17.11 |
| 4,642,121 A | * | 2/1987 | Keller | 623/22.12 |
| 4,713,006 A | * | 12/1987 | Hakamatsuka et al. | 433/201.1 |
| 5,534,028 A | * | 7/1996 | Bao et al. | 623/17.16 |
| 5,683,464 A | * | 11/1997 | Wagner et al. | 623/17.16 |
| 5,836,949 A | * | 11/1998 | Campbell et al. | 606/62 |
| 6,447,547 B1 | * | 9/2002 | Michelson | 623/17.16 |
| 6,554,778 B1 | * | 4/2003 | Fleming, III | 600/567 |
| 2001/0018616 A1 | * | 8/2001 | Schwab | 623/23.17 |
| 2002/0029082 A1 | * | 3/2002 | Muhanna | 623/17.11 |
| 2003/0028249 A1 | * | 2/2003 | Baccelli et al. | 623/17.11 |
| 2003/0036798 A1 | * | 2/2003 | Alfaro et al. | 623/17.16 |
| 2003/0229398 A1 | * | 12/2003 | Iesaka | 623/22.17 |

* cited by examiner

*Primary Examiner*—Pedro Philogene
*Assistant Examiner*—David A. Bonderer
(74) *Attorney, Agent, or Firm*—Dilworth & Barrese, LLP

(57) ABSTRACT

The present invention is directed to an impact-absorbing member for use with an implant insertion instrument and the placement of an implant in a recipient's body. Preferably, the implant is a spinal implant for insertion into the intervertebral space. The impact-absorbing member may be attached to the implant insertion instrument, the implant, or both. The impact-absorbing member reduces the impact forces on the implant during placement.

4 Claims, 3 Drawing Sheets

BIO-IMPLANT INSERTION INSTRUMENT

CROSS REFERENCE TO RELATED APPLICATIONS

This application claims the benefit under 35 U.S.C. §119(e) of earlier filed and copending U.S. Provisional Application No. 60/370,015, filed Apr. 4, 2002, the contents of which are incorporated by reference herein.

BACKGROUND OF THE INVENTION

1. Technical Field

The present invention relates generally to implants and to implant insertion instruments. More particularly, the present invention relates to implants and implant insertion instruments having impact absorption elements adapted to reduce the impact forces realized on an implant during the placement of the implant into a bony defect or deficit. In a preferred embodiment, the implant is a spinal implant which is placed into a receiving bed formed in an intervertebral space.

2. Background of Related Art

The use of implants for the repair of bony sites in the body is known to those skilled in the art. Implants are formed of a variety of different biologically compatible materials including metals (e.g., stainless steel, titanium, etc.), ceramics, polymers, human or animal bone, including cancellous or cortical bone, and composites. Unlike an implant constructed from metal, an implant constructed from cancellous bone can not be used just anywhere in the body due to its reduced mechanical strength. As such, implants constructed entirely from cancellous bone are generally used in areas subjected to reduced levels of mechanical stress. In contrast, implants constructed entirely from cortical bone have the mechanical strength suitable for use in any load-bearing region of the body. Accordingly, depending on the intended site for implantation, implants may be constructed of different materials tailored to the characteristics most desired at the site of implantation, e.g., mechanical strength, osteoinduction, etc.

For example, intervertebral implants for fusing together adjacent vertebrae of the spinal column are well known in the art. Such implants are formed in a variety of different shapes and sizes and are configured for insertion into receiving beds formed in the various regions of the spine. Intervertebral implants are formed of a variety of different biologically compatible materials including metals (e.g., stainless steel, titanium, etc.), ceramics, polymers, human or animal bone, including cancellous or cortical bone, and composites. Due to its reduced mechanical strength, an implant constructed from cancellous bone can not be used in all locations in the spinal column. As such, implants constructed entirely from cancellous bone are generally used in the cervical region of the spine. In contrast, implants constructed entirely from cortical bone have the mechanical strength suitable for use in any region of the spine. However, due to its osteoconductive properties, it is more desirable to use a spinal implant constructed from cancellous bone where possible, than a spinal implant constructed from cortical bone.

Intervertebral bone implants should stabilize the intervertebral space and become fused to adjacent vertebrae. Further, during the time it takes for fusion, i.e. biological fixation of the vertebrae, to be completed, the implant should have enough structural integrity to maintain the intervertebral space without substantial degradation or deformation of the implant. The implant must also provide spinal load support between the vertebrae.

When mineralized bone is used in grafts, it is primarily because of its inherent strength, i.e., its load bearing ability at the recipient site. While bone offers much improved incorporation, the inherent brittle nature of bone resulting from a high mineral content, particularly load-bearing cortical bone, severely limits its potential deformation. This has led to the development of surface demineralized bone grafts. Surface demineralization helps the graft to conform to the surgical site, and may also advantageously increase the rate of bone incorporation.

The process of demineralizing bone grafts is well known in the art. The successful application of such bone is predicated on sound knowledge of its biologic properties and its capacity to withstand the stresses to which it will be subjected. Demineralizing bone, using for example, a controlled acid treatment, increases the osteoinductive characteristics of the bone graft. One downside of the demineralization process is that the bone graft loses mechanical strength during the demineralization process. Demineralization of an implant can result in a reduction of its mechanical strength (e.g., in its compressive strength) depending on the configuration of the implant. Depending on the depth of the demineralization zone, this reduction in mechanical strength can range in degree from the negligible to the point where the implant is no longer suitable for its intended application.

In addition, some bone treatment processes, such as irradiation and lyophilization, can work against conservation of the mechanical strength of bone and can lessen the bone's weight bearing properties.

In some cases, instruments are utilized to aid in the positioning and placement of implants into a recess or defect present in bone. For example, the placement of a bone implant between adjacent vertebrae can be quite difficult. The implant is contoured to fit into the intervertebral space between the adjacent vertebrae after removal of the damaged intervertebral disk. During the insertion phase of the procedure, the implant typically will be held with a clamp, forceps, or some other such device in order to place the implant into the entry of the disc space. The implant is then usually engaged by a rod or punch, the end of which is tapped by a mallet, which drives the implant into the disc space. Implants that are impacted into place are subjected to high peak loads from the impacting operation. Even moderate hammering can generate loads of several thousand pounds, and can cause cracking or breaking of the implant. The effects of the hammering are further evident when a partially demineralized bone implant, having reduced mechanical strength, is used.

Instruments for positioning implants in a receiving bed, including but not limited to a bed formed between adjacent vertebrae, include instruments for gauging the size of a receiving bed, instruments for grasping an implant, and instruments for driving an implant into the receiving bed. A common deficiency in each of these instruments is that they treat all implants as if they are made of metal, thereby leading to the application of excessive insertion forces on bone implants. When these surgical instruments are used for insertion of implants constructed from bone, these instruments can cause the implant to weaken, crack, or even splinter during the insertion procedure, which seriously complicates the surgical procedure. These complications may lead to a total failure of the implant and/or a significant decrease in obtaining a solid bony arthrodesis. Moreover, an entirely new implant may be required if damage to the implant is excessive.

Accordingly, a need exists for a series of improved implant insertion instruments which are configured to facilitate ease of insertion of a bone implant into an implant receiving bed, and which decrease the impact load applied to the implant during insertion. Such instruments are especially needed in the area of spinal surgery, to facilitate the insertion of an implant into the intervertebral space and decrease the risk of damage to the implant.

SUMMARY OF THE INVENTION

The present invention is directed to implant insertion instruments possessing a handle portion, a head portion having an implant-impacting end, an elongated body portion interconnecting the head portion and handle portion, and an impact-absorbing member affixed to at least a portion of the implant-impacting end of the head portion of the implant insertion instrument.

In one embodiment, the head portion of the implant insertion instrument possesses a conical body portion having an implant-impacting end formed at a smaller end of the conical body portion and a second implant-impacting end formed at a larger end of the conical body portion. In this embodiment, an impact-absorbing member may be affixed to at least a portion of both the implant-impacting end at the smaller end of the conical body portion and the second implant-impacting end at the larger end of the conical body portion.

The present invention is also directed to implants possessing an enhanced ability to withstand impact forces applied during insertion of the implant into a recipient. Such implants have an impact-absorbing member affixed thereto The present invention is also directed to a method for reducing impact forces on an implant during placement of the implant into a bony defect or void in a recipient by inserting an impact-absorbing member between an implant-impacting end of an implant insertion instrument and the implant. The impact-absorbing member may simply be placed between the implant-impacting end of the implant insertion instrument and the implant, or it may be affixed to the implant-impacting end of the implant insertion instrument, the implant, or both.

The impact-absorbing member may be temporarily attached to the implant insertion instrument during insertion by means of a non-permanent adhesive, a strap, or a band. In one embodiment, the impact-absorbing member is configured to interlock with the implant-impacting end of the implant insertion instrument to temporarily attach the impact-absorbing member to the implant insertion instrument.

The impact-absorbing member may also be temporarily attached to the implant by means of a non-permanent adhesive, a strap, or a band. Here again, the impact-absorbing member may be configured to interlock with an exposed surface of the implant to temporarily attach the impact-absorbing member to the implant.

The impact-absorbing member may be permanently attached to the implant insertion instrument by injection molding, screws, rivets, or permanent adhesives.

The impact-absorbing member may also be permanently attached to the implant by injection molding, screws, rivets, or permanent adhesives. Where the impact-absorbing member is permanently attached to the implant, the impact-absorbing member should be constructed of biocompatible materials which, in some embodiments, are biodegradable.

The impact-absorbing member may also be permanently attached to the implant and temporarily attached to the implant insertion instrument, or temporarily attached to the implant and permanently attached to the implant insertion instrument. In one embodiment, the impact-absorbing member is temporarily attached to both the implant insertion instrument and the implant. Where the impact-absorbing member is attached to both the implant and the implant insertion instrument, the impact-absorbing member attaches the implant to the implant insertion instrument during insertion and aids in the placement of the implant in the recipient.

In a preferred embodiment, the implant is an intervertebral implant.

BRIEF DESCRIPTION OF THE DRAWINGS

By way of example only, preferred embodiments of the disclosure will be described with reference to the accompanying drawings, in which.

DETAILED DESCRIPTION OF THE INVENTION

Figure 1:
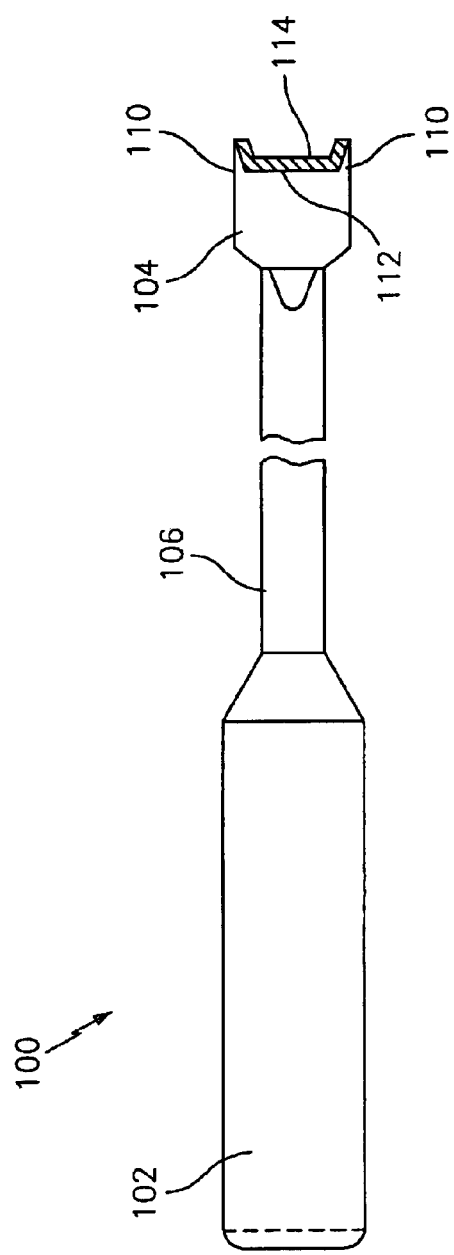
FIG. 1 is a side elevational view of an embodiment of an implant insertion instrument according to the present disclosure.

Implant insertion instruments according to the present disclosure are intended to be used during bone implant procedures, e.g., spinal fusion surgery, and are especially suited for procedures where it is desirable to decrease the incidence of implant fracture during surgery. Although the majority of this disclosure refers to spinal fusion surgery, the instruments according to the present disclosure are entirely suitable to applications involving the repair of other bony sites in the body where the instruments are utilized to decrease an impact load applied to the bone implant during the placement of the implant in a recipient.

Bone implants that are impacted into place are subjected to high peak impact loads from the impacting operation. Even moderate hammering can generate loads of several thousand pounds, and can cause cracking or breaking of the implant. In accordance with the present invention, peak impact loads to small areas of the implant are limited by inserting an impact-absorbing member (e.g., an elastomeric pad) between the implant-impacting end of the implant insertion instrument and the impacted surface of the implant. The impact-absorbing member absorbs, then releases energy, thereby spreading the loading evenly over the entire impacted surface for a longer time period. The total force delivered to the implant remains the same, except for a tiny amount of energy dissipated as heat by the impact-absorbing member. Thus, for example, doubling the time to deliver the force of a hammer blow cuts the peak load in half.

The impact-absorbing member may simply be placed between the implant and implant insertion instrument and subsequently removed from a recipient's body. Alternatively, the impact-absorbing member may be temporarily or permanently attached to an implant-impacting end of an implant insertion instrument, an implant, or both. The placement of the impact-absorbing member between the implant insertion instrument and the implant reduces peak forces on the implant when the implant insertion instrument comes into contact with the implant. It is also possible to incorporate the impact-absorbing member in a hammer to be applied to an impact end of an instrument or internally in the implant insertion instrument.

Where the impact-absorbing member is permanently attached to the implant and will be retained in the implant recipient's body, the impact-absorbing member must be constructed of biocompatible materials. As used herein, the term "biocompatible" and expressions of like import shall be understood to mean the absence of stimulation of an unacceptable biological response to an impact-absorbing member present on an implant and is distinguished from a mild, transient inflammation and/or granulation response which can accompany implantation of most foreign objects into a living organism and is also associated with the normal healing response. Materials useful to the invention herein shall be biocompatible if, at the time of implantation, they are present in a sufficiently small concentration such that the above-defined condition is achieved.

In addition, where the impact-absorbing member is permanently attached to the implant and will be retained in the implant recipient's body, the impact-absorbing member may preferably be constructed of biodegradable materials. As used herein, the terms "biodegradable", "bioerodible", and expressions of like import used with respect to impact-absorbing members mean that the impact-absorbing member is broken down gradually by the body after implantation. After a period of time, which may vary depending upon various factors such as the thickness of the impact-absorbing member, the components of the impact-absorbing member, and the specific use of the impact-absorbing member, the impact-absorbing member loses its unitary structure. For example, the impact-absorbing member may break into pieces, and may eventually be completely resorbed. Preferably, the impact-absorbing member is bioabsorbable in addition to being biodegradable; i.e., the impact-absorbing member is resorbed by the body such that the impact-absorbing member becomes essentially non-detectable at the site of implantation. The term "biodegradable" as used herein encompasses the complete resorption of the impact-absorbing member by the body as well as a breakdown of the impact-absorbing member without complete resorption of the pad; i.e., the structure of the impact-absorbing member is broken down into a plurality of pieces which are not completely resorbed.

A further advantage of using an impact-absorbing member at the instrument/implant interface is to more evenly load the implant. For example, an implant formed of cancellous bone contains a number of minor irregularities such that there is never perfect contact over 100% of the instrument/implant interface. In other words, while the instrument surface is generally perfectly planar, the implant surface is not. As such, the initial implant impact loading is localized over a few peak spots on the implant surface that then experience a very high loading. As a result of these initially highly loaded areas, the implants are more likely to experience local failure that can lead to crack propagation and splitting of the implant. Therefore, a soft pad at the instrument/implant interface greatly reduces the peak loads on these irregular areas.

Preferred embodiments of the presently disclosed implant insertion instruments will now be described in detail with reference to the drawings in which like reference numerals designate identical or corresponding elements in each of the several views.

FIG. 1 illustrates an implant insertion instrument according to the present disclosure shown generally as 100. The implant insertion instrument 100 includes a handle portion 102, a head portion 104 and an elongated body portion 106 interconnecting the head portion 104 and handle portion 102. According to the embodiment of FIG. 1, the head portion 104 includes a pair of spaced apart angled extensions 110 defining a recess 112 in the implant-impacting end of the head portion 104. The recess 112 is configured and adapted to mate with a correspondingly shaped surface of an intervertebral implant (not shown). In this manner, the angled extensions 110 prevent the implant-impacting end of head 104 from slipping off of a side of the implant. In addition, the recess 112 of implant-impacting end of the head 104 is provided with an impact-absorbing member 114 affixed thereto which conforms in shape to the recess 112. The impact-absorbing member 114 provides a cushion where the implant-impacting end of the head portion 104 contacts the intervertebral implant to reduce wear, deformation, and the risk of fracture of the implant.

Figure 2:
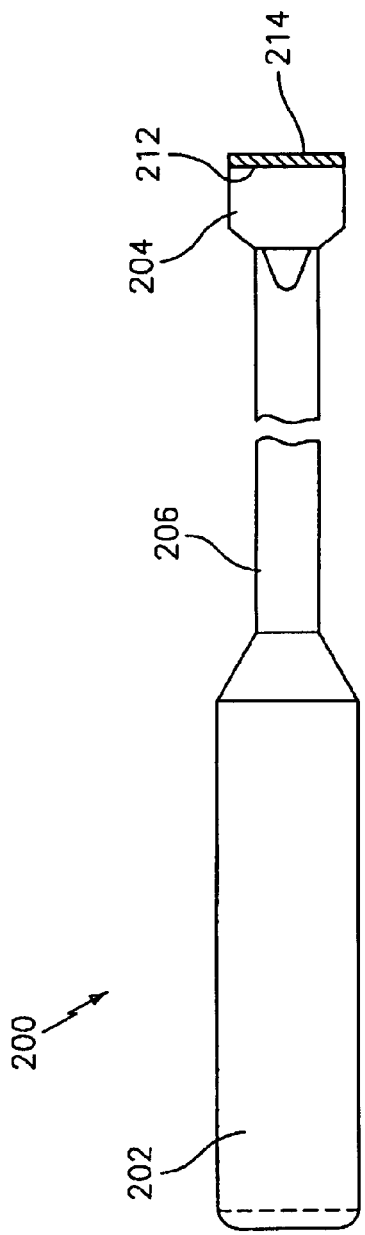
FIG. 2 is a side elevational view of an alternative embodiment of the implant insertion instrument shown in FIG. 1.

Turning now to FIG. 2, an implant insertion instrument according to an alternative embodiment of the present disclosure is shown generally as 200. The implant insertion instrument 200 includes a handle portion 202, a head portion 204 and an elongated body portion 206 interconnecting the head portion 204 and handle portion 202. In addition, an implant-impacting end 212 of the head 204 is provided with an impact-absorbing member 214 affixed, which impact-absorbing member 214 provides a cushion along the interface between the implant-impacting end 212 of the head portion 204 and an intervertebral implant having a substantially planar surface.

In use, with the implant generally in place, the implant-impacting ends of the heads of each of the implant insertion instruments 100 and 200 are brought into contact with an exposed surface of the implant. With the instruments 100 and 200 in place, a hammering device (not shown) is used to impact an end surface of each of the handles 102 and 202 respectively. The impact force is transmitted through the implant instruments 100 and 200 to the implant itself. However, with the introduction of the impact-absorbing members 114 and 214 the peak impact force being transmitted through the implant instruments 100 and 200 is reduced.

Figure 3:
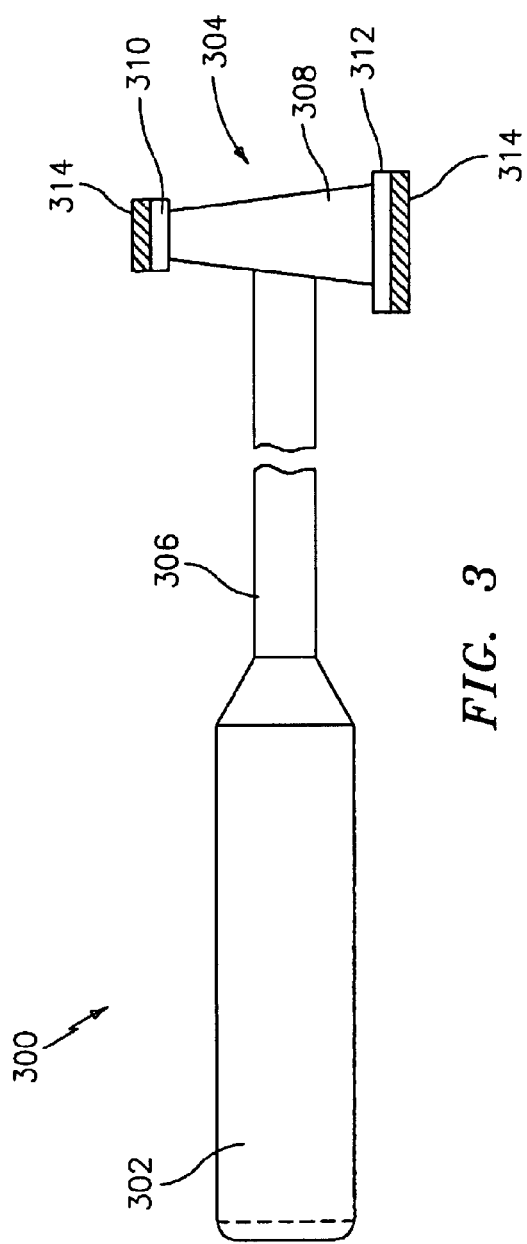
FIG. 3 is a side elevational view of another implant insertion instrument according to the present disclosure.
Figure 4:
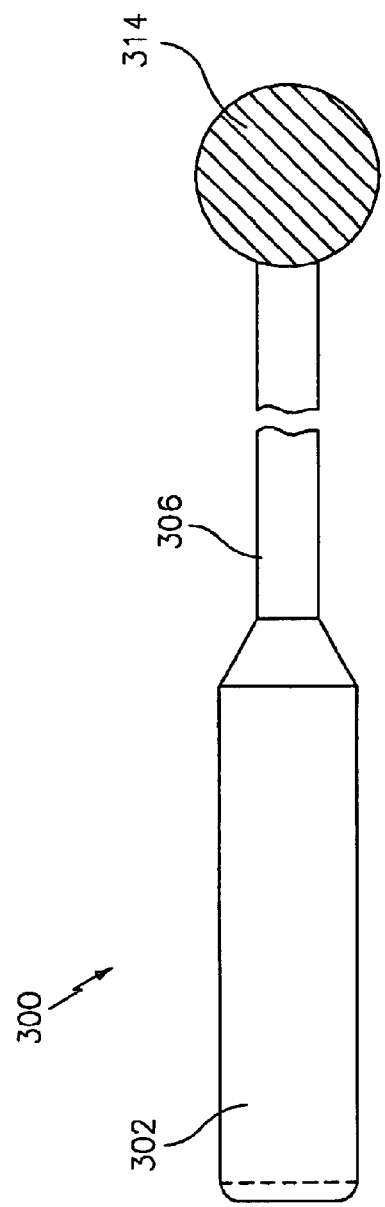
FIG. 4 is a top plan view of the implant insertion instrument as shown in FIG. 3.

Turning now to FIGS. 3 and 4, an implant insertion instrument according to an alternative embodiment is generally shown as 300. The implant insertion instrument 300 includes a handle portion 302, a head portion 304 and an elongated body portion 306 interconnecting the head portion 304 and handle portion 302. The head portion 304 includes a conical body portion 308 having a smaller implant-impacting end 310 formed at the smaller end of the conical body portion 308 and a larger implant-impacting end 312 formed at the larger end of the conical body portion 308. In addition, each implant-impacting end 310 and 312 is provided with an impact-absorbing member 314 affixed thereto, which impact-absorbing member 314 provides a cushion along the interface between the implant-impacting ends 310 and 312 of the head portion 304 and an intervertebral implant. As seen in FIG. 4, the implant-impacting end 312 and corresponding impact-absorbing member 314 is circular, however, it is envisioned that any shape implant-impacting end and pad can be used.

The implant insertion instrument 300 is primarily used to directly impact an intervertebral implant. With the implant partially in place between adjacent vertebrae (i.e., within the intervertebral space) the implant insertion instrument is used to directly strike or impact the implant. Use of a conventional implant insertion instrument to directly strike the implant can result in a cracking and/or a splintering of the implant itself. As such, according to the present disclosure, the implant insertion instrument 300 is provided with an impact-absorbing member 314 on each of its implant-impacting ends 310 and 312 to thereby reduce the peak impact force being transmitted to the implant.

The present invention also is directed to implants having an impact-absorbing member affixed thereto. Such implants, possessing an impact-absorbing member, have the ability to withstand the impact forces applied during placement of the implant into a bony defect or deficit. Suitable implants may be made of any material commonly used in the construction of implants. Preferably, the implants may be made of bone, including cancellous, cortical, cortico-cancellous, mineralized, demineralized (including partially or surface demineralized) and combinations thereof. As used herein, the term "demineralized" refers to bone containing less than about 95% of its original mineral content and the expression "fully demineralized" refers to bone containing less than about 5% of its original mineral content.

Figure 5:
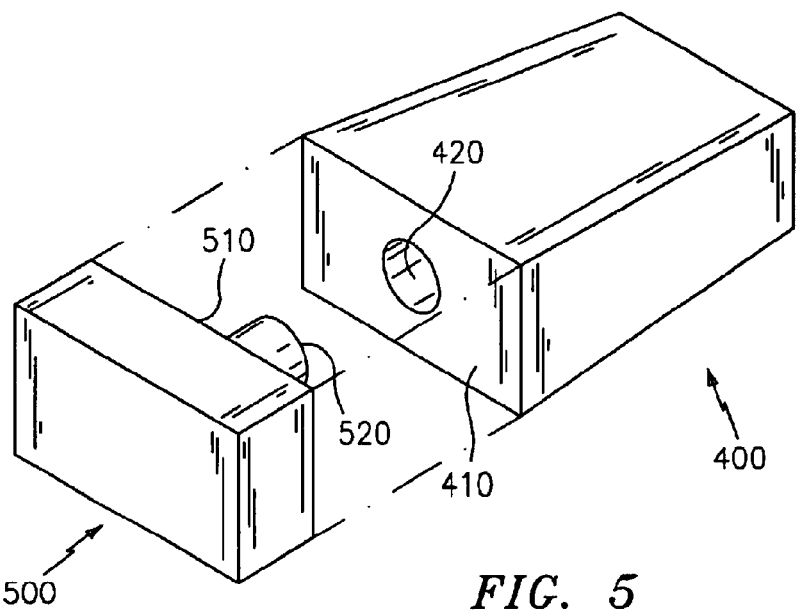
FIG. 5 is a side view of an implant and impact-absorbing member in accordance with the present invention prior to the attachment of the impact-absorbing member to the implant.

FIG. 5 illustrates an implant and impact-absorbing member for use therewith according to the present disclosure. The implant 400 includes an impact-receiving surface 410. The impact-absorbing member 500 possesses an implant-contacting surface 510. Impact-receiving surface 410 of the implant possesses a recess 420 configured and adapted to mate with a correspondingly shaped protrusion 520 from implant-contacting surface 510 of impact-absorbing member 500. FIG. 5 depicts the implant 400 and impact-absorbing member 500 separately, prior to their being affixed together. In an alternative embodiment (not depicted), implant-contacting surface 510 of impact-absorbing member 500 possesses a recess configured and adapted to mate with a correspondingly shaped protrusion from impact-receiving surface 410 of implant 400.

Figure 6:
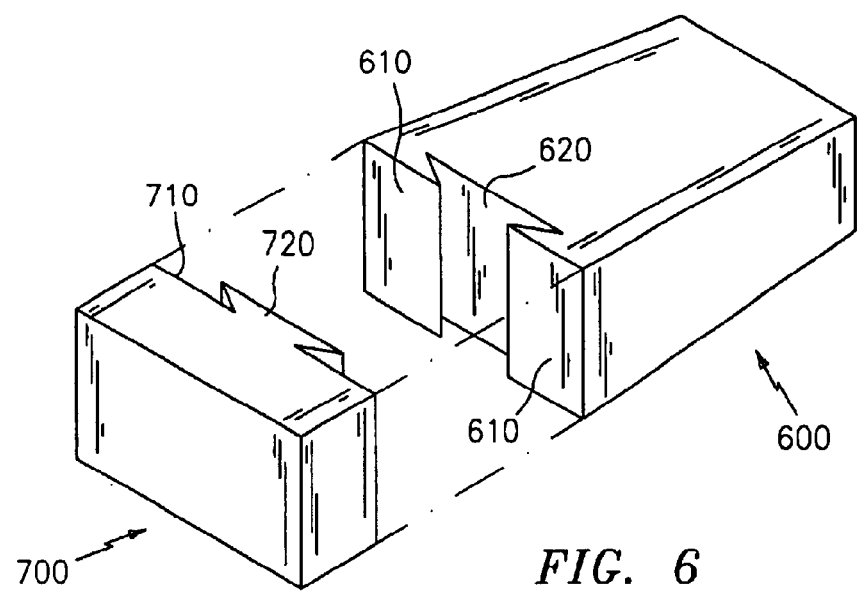
FIG. 6 is a side view of an alternative embodiment of an implant and impact-absorbing member in accordance with the present invention prior to the attachment of the impact-absorbing member to the implant.

FIG. 6 depicts an alternate embodiment of an implant and impact-absorbing member for use therewith according to the present disclosure. The implant 600 includes an impact-receiving surface 610. The impact-absorbing member 700 possesses an implant-contacting surface 710. Impact-receiving surface 610 of the implant possesses a slot 620 configured and adapted to mate with a correspondingly shaped projection 720 from implant-contacting surface 710 of impact-absorbing member 700. FIG. 6 also depicts the implant 600 and impact-absorbing member 700 separately, prior to their being affixed together. In an alternative embodiment (not depicted), implant-contacting surface 710 of impact-absorbing member 700 possesses a slot configured and adapted to mate with a correspondingly shaped projection from impact-receiving surface 610 of implant 600.

Preferably, the implants of the present invention are intervertebral implants for insertion in the intervertebral space. However, implants of the present invention may be used in the repair of other conditions including, but not limited to, ligament repair, joint repair or replacement, non-union fractures, facial reconstruction and spinal stabilization.

The impact-absorbing member may be supplied sterile in a separate package as a one time use disposable item. If supplied separately, the impact-absorbing members in any of the above disclosed embodiments may simply be placed between the impact surface of the implant instrument and the implant.

In another embodiment, the impact-absorbing member may be temporarily affixed to the implant-impacting end of the insertion instrument, an exposed surface of the implant, or both, by non-permanent adhesives (e.g., rubber cement) or by the use of straps or bands (not shown) extending from the edges of the impact-absorbing members and fitting over the underlying supporting members of the implant insertion instrument or implant. For attachment to an implant insertion instrument, the attachment to the underlying supporting members as set forth in the Figures would be the heads 104 and 204 (FIGS. 1 and 2), and the implant-impacting ends 310 and 312 of the head 304 (FIGS. 3 and 4).

In addition, the impact-absorbing member may be configured to interlock with the surface of the implant insertion instrument to temporarily attach the impact-absorbing member thereto. For example, the impact-absorbing member may have a plug or nipple configuration on its surface adjacent to the surface of the implant insertion instrument which, in turn, possesses a receptacle for receipt of the plug or nipple so that the pad is capable of interlocking with the surface of the implant insertion instrument. Such a configuration may be utilized to temporarily attach the impact-absorbing member to the implant insertion instrument, as the elastomeric nature of the pad will permit removal of the pad from the surface of the implant insertion instrument. A similar configuration may be utilized to temporarily attach an impact-absorbing member to an implant. In one embodiment, the impact-absorbing member may be temporarily affixed to both the implant and the implant insertion instrument surface by being configured to interlock with both the implant and the implant insertion instrument surface. In such a case, where it is not intended for the impact-absorbing member to remain attached to the implant and remain within the recipient's body, it should be easier to detach the impact-absorbing member from the implant than to detach the impact-absorbing member from the implant insertion instrument. In this way, subsequent to placement of the implant, the impact-absorbing member may be detached from the implant while remaining attached to the implant insertion instrument.

Retaining grooves may be engineered into the implant insertion instrument and/or the impact-absorbing member in order to prevent the pad from detaching from the implant insertion instrument as the implant insertion instrument is removed from the implant. Similarly, where it is intended that the impact-absorbing member remain within the recipient's body after implantation, retaining grooves may be engineered into the implant and/or the impact-absorbing member in order to prevent the pad from detaching from the implant as the implant insertion instrument is removed from the implant.

In another embodiment, the impact-absorbing member may be permanently attached to the implant insertion instrument or the implant. Means for permanently attaching the impact-absorbing member to the implant or implant insertion instrument are known to those skilled in the art and include, but are not limited to, injection molding, screws, rivets and permanent adhesives.

For example, the impact-absorbing member may be permanently attached to the implant insertion instrument by molded tabs or protrusions that engage with recesses in the instrument head (or by tabs or protrusions on the instrument head that engage with recesses in the impact-absorbing member, these may be at the implant-interface surface or in a region away from the implant-interface surface), by recessed screws, or screws separate from the implant-interface surface. The impact-absorbing member may also be permanently attached to the implant or implant insertion instrument by slots or recesses in the impact-absorbing member that engage with slots or recesses in the implant or implant insertion instrument.

Where the impact-absorbing member is permanently affixed to the implant itself, it is preferred that the impact-absorbing member be made of biocompatible materials. In such a case, the impact-absorbing member is preferably bioerodible and biodegradable. In this manner, conventional implant insertion instruments (i.e., without padding) can be used to impact the implant into place.

In some embodiments, it may be preferable to attach the impact-absorbing member to both the implant and the implant insertion instrument. Where the impact-absorbing member is attached to both the implant and the implant insertion instrument, the impact-absorbing member serves as a means for attaching the implant to the implant insertion instrument during insertion and aids in the placement of the implant in the recipient.

For example, if the impact-absorbing member has been temporarily affixed to the implant insertion instrument, it may be permanently or temporarily attached to the implant, and where the impact-absorbing member has been permanently affixed to the implant insertion instrument, it may be temporarily attached to the implant. By attaching the impact-absorbing member to both the implant and implant insertion instrument, placement of the implant in the recipient is greatly facilitated.

In one preferred embodiment, the impact-absorbing member is attached to both the implant insertion instrument and the implant itself, and thus may be able to attach the implant to the implant insertion instrument during implantation. In such a case, the impact-absorbing member must be temporarily attached as discussed above to the implant, the implant insertion instrument, or both. So, for example, the impact-absorbing member may be permanently attached to the implant insertion instrument and temporarily attached to the implant, or temporarily attached to the implant insertion instrument and permanently attached to the implant. As noted above, in those cases where the impact-absorbing member is permanently attached to the implant, the impact-absorbing member should be made of biocompatible materials.

The impact-absorbing members in any of the above disclosed embodiments may be formed of any polymeric material suitable for contact with an implantable device. Suitable materials include, but are not limited to, polyethylene, polypropylene polyvinylchloride (PVC) with or without impact modifiers, EPDM, styrene-isoprene-styrene, styrene-butadiene-styrene, styrene-ethylene-butylene-styrene, ethylene alpha-olefin rubber, ethylene propylene diene monomer rubber, butyl rubber, vulcanized natural rubber, urethanes, silicone rubber, stiff gels, and combinations thereof. The materials utilized should be sterilizable, and resistant to the shedding of particles therefrom. The thickness and hardness of the impact-absorbing members may be tailored to the particular surgical application in which it is intended to be used. The impact-absorbing members may be flat, or may have features machined into it that will fit specific features of an implant. For example, if the implant has an anti-rotation groove on its surface, a corresponding tang may be incorporated into the pad.

A further advantage of an impact-absorbing member at the implant insertion instrument/implant interface is that it loads the implant more evenly. Due to minor irregularities there may be imperfect contact over 100% of the implant insertion instrument/implant interface, which means that the initial implant loading is localized over a few spots, that then experience very high loading. As the bone deforms under the load, the force becomes more evenly distributed. However, the initially highly loaded areas are more likely to experience local failure that can lead to crack propagation. The elastomeric pad at the implant insertion instrument/implant interface greatly reduces the peak loads on the irregular areas.

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization.

Various modifications may be made to the embodiments disclosed herein. For example, any material having the requisite strength requirements which are suitable for surgical use may be used to construct the implant insertion instrument including, but not limited to, surgical grade stainless steel, plastics, etc. Moreover the size of the implant insertion instrument and/or the impact-absorbing member may be changed to suit a particular surgical procedure, e.g., cervical spinal fusion, lumbar spinal fusion, thoracic spinal fusion, etc. Therefore, the above description should not be construed as limiting, but merely as exemplifications of, preferred embodiments. Those skilled in the art will envision other modifications within the scope and spirit of the present disclosure.

What is claimed is:

1. An implant possessing enhanced ability to withstand impact forces comprising:

a) an implant made of bone; and, b) an impact-absorbing member permanently affixed to an exposed surface of the implant, said impact-absorbing member absorbing, then releasing, impact energy applied thereto thereby spreading the impact energy evenly over the entire impacted surface of the implant for a longer period of time than were the impact energy applied directly to the implant.

2. The implant of claim 1 wherein the implant possesses a configuration which mates with a correspondingly shaped receiving configuration on the impact-absorbing member.

3. The implant of claim 1 wherein the implant is an intervertebral implant.

4. The implant of claim 1 wherein the impact-absorbing member is permanently attached to the implant by injection molding, screws, rivets, or a permanent adhesive.

* * * * *